United States Patent
Huang

(10) Patent No.: US 6,689,396 B2
(45) Date of Patent: Feb. 10, 2004

(54) SKIN CARE PRODUCT CONTAINING POWDER OF EVENING PRIMROSE

(76) Inventor: Wen Tzu Huang, No. 1112-1, Jea How Rd., How Lii Shiang, Taichung Hsien (TW)

( * ) Notice: Subject to any disclaimer, the term of this patent is extended or adjusted under 35 U.S.C. 154(b) by 236 days.

(21) Appl. No.: 09/996,412

(22) Filed: Nov. 19, 2001

(65) Prior Publication Data

US 2003/0095942 A1 May 22, 2003

(51) Int. Cl.$^7$ .................. A61K 35/78; A61K 7/055; A61K 9/14; A61K 7/50; A61K 7/48
(52) U.S. Cl. .................. 424/725; 424/69; 424/400; 424/401; 424/405; 424/489; 510/130; 510/139; 510/159; 514/783; 514/846; 514/937
(58) Field of Search .................. 424/400, 401, 424/489, 405, 69, 725; 514/783, 846, 937; 510/130, 139, 159

(56) References Cited

U.S. PATENT DOCUMENTS 5,578,312 A * 11/1996 Parrinello .................. 424/401
6,274,176 B1 * 8/2001 Tomer et al. ............... 424/725

* cited by examiner

*Primary Examiner*—Michael G. Hartley
*Assistant Examiner*—Marina Lamm
(74) *Attorney, Agent, or Firm*—Pro-Techtor International Services

(57) ABSTRACT

A skin care product is formed of 1–10% by weight of an evening primrose powder with a particle size raning between 70 and 150 mesh, 89.9–98.6% by weight of a solid, liquid, or powered detergent base, and 0.1–0.4% by weight of a prfume. The skin care product is effetive in cleansing skin without injuring the skin. The evening primrose powder contains linolenic acid which is capable of reducing the contents of sugar and fat of the blood. The particles of the evening primrose powder are capable of a direct friction with the skin, thereby resulting in an effective removal of dead skin cells, skin cutin, and skin filth.

7 Claims, No Drawings

SKIN CARE PRODUCT CONTAINING POWDER OF EVENING PRIMROSE

FIELD OF THE INVENTION

The present invention relates generally to a skin care product, and more particularly to a cleansing product capable of cleansing skin effectively and improving the appearance of the skin.

BACKGROUND OF THE INVENTION

There are a variety of skin care products available in the market place today. These conventional skin care products are intended to improve the appearance of the skin by removing the dead skin cells, the skin cutin, and the filth deposited on the skin. The conventional skin care products contain the quartz powder, the scent, and the cleansing substance such as detergent; nevertheless they are not effective in caring and beautifying the skin. In addition, the skin is susceptible to bruise, which is caused by the quartz powder or plastic powder contained in the conventional skin care products.

SUMMARY OF THE INVENTION

The primary objective of the present invention is to provide a skin care product which is free of the shortcomings of the conventional skin care product described above.

In keeping with the principle of the present invention, the foregoing objective of the present invention is attained by the skin care product which is formed of 1–10% by weight of an evening primrose powder, 89.9–98.6% by weight of a detergent base, and 0.1–0.4% by weight of a perfume. The evening primrose powder has a particle size ranging between 70 and 150 mesh.

The skin care product of the present invention takes the form of solid, liquid, or powder, depending on the form of the detergent base. The particles of the evening primrose powder are effective in removing the dead skin cells, the skin cutin, and the skin filth without causing the skin bruise. The evening primrose powder contains linolenic acid which is capable of reducing the contents of sugar and fat of the blood.

The present invention will be more readily understood upon a thoughtful deliberation of the following detailed description of the embodiments.

EMBODIMENT 1

The skin care product of the first preferred embodiment of the present invention takes the solid form and contains 1–10% by weight of an evening primrose powder, 89.9–98.6% by weight of a solid detergent base, and 0.1–0.4% by weight of apple essence. The particle size of the evening primrose powder ranges between 70 and 100 mesh.

The solid detergent base is formed of 20% by weight of sodium ethyl alcohol sulfate, 9% by weight of Chromium Dehydrate Enzyme Hydrocarbonyl Sulfonate, 5% by weight of alcohol amide, 5% by weight of soap, 6% by weight of fatty acid, 3% by weight of water, and 2% by weight of other ingredients.

There are two kinds of composition of the solid detergent base referred to above. They are described as follows:

A. 3% weight of sodium benzyl alkyl sulfate; 45% by weight of Acylglutathiona Soda; 16% by weight of soap; 31% by weight of fatty acid; 1% by weight of table salt; 2.5% by weight of water; 1.5% by weight of other ingredients.

B. 75 parts of tallow candle; 15 parts of coconut oil; 10 parts of rice bran oil; 14.6 parts of water; 0.5 part of pigment.

EMBODIMENT 2

The skin care product of the second preferred embodiment of the present invention takes the liquid form and contains 1–10% by weight of an evening primrose powder, 89.9–98.6% by weight of a liquid detergent base, and 0.1–0.4% by weight of banana essence. The particle size of the evening primrose powder ranges between 70 and 120 mesh.

The liquid detergent base is formed of the following oil phase and water phase.

The oil phase includes 6600 parts of stearic acid, 1925 parts of cetyl alcohol, 2420 parts of methyl glucoside sesquistearate (G.M.S. emulsifier), 80 parts of propyl p-hydroxybenzoate.

The water phase includes 2200 parts of glycerin, 1200 parts of Dodecathyl Benzene (70), 80 parts of methyl p-hydroxybenzoate, 300 parts of potassium hydroxide, and 4111 parts of distilled water.

The water phase and the oil phase are heated to reach 75° C. before the water phase is poured into the oil phase. The water phase and the oil phase are stirred at a high speed to emulsify and are then cooled to 45° C. at which 30 parts of a bactericidal agent are added.

EMBODIMENT 3

The skin care product of the third preferred embodiment of the present invention takes the powdered form and contains 1–10% by weight of an evening primrose powder, 89.9–98.6% by weight of a powdered detergent base, and 0.1–0.4% by weight of pineapple essence. The particle size of the evening primrose powder ranges between 90 and 120 mesh.

The powdered detergent base contains 75 parts of wheat powder, 15 parts of kaolin, 0.65 part of Aerosol-type surfactant, 7 parts of boron sand, 2 parts of silicon dioxide, and 0.35 part of pigment.

The embodiments of the present invention described above are nonrestrictive. Accordingly, the present invention may be embodied in other specific forms without deviating from the spirit thereof. The present invention is therefore to be limited only by the scopes of the following claims.

What the invention claimed is:

1. A skin care product containing 1–10% by weight of an evening primrose powder having a particle size ranging between 70 and 150 mesh, 89.9–98.6% by weight of a detergent base, and 0.1–0.4% by weight of a perfume.

2. The skin care product as defined in claim 1, wherein said detergent base is a solid detergent base.

3. The skin care product as defined in claim 2, wherein said evening primrose powder has a particle size ranging between 70 and 100 mesh; wherein said solid detergent base is formed of 20% by weight of sodium ethyl alcohol sulfate, 9% by weight of Chromium Dehydrate Enzyme Hydrocarbonyl Sulfonate, 5% by weight of alcohol amide, 5% by weight of soap, 6% by weight of fatty acid, 3% by weight of table salt, 5% by weight of water, and 2% by weight of other ingredients; and wherein said perfume is apple essence.

4. The skin care product as defined in claim 1, wherein said detergent base is a liquid detergent base.

5. The skin care product as defined in claim 4, wherein said evening primrose powder has a particle size ranging between 70 and 120 mesh; wherein said liquid detergent base has an oil phase and a water phase, with said oil phase comprising 6600 parts of stearic acid, 1925 parts of cetyl alcohol, 2420 parts of methyl glucoside sesquistearate (G.M.S emulsifier), 80 parts of propyl p-hydroxybenzoate, said water phase comprising 2200 parts of glycerin, 1200 parts of 12 Dodecathyl Benzene (N70), 80 parts of methyl p-hydroxybenzoate, 300 parts of potassium hydroxide, and 4111 parts of distilled water whereby said water phase and said oil phase are heated to reach 75° C. before said water phase is poured into said oil phase, said water phase and said oil phase being then stirred at a high speed to emulsify before being cooled to 45° C. at which 30 parts of a bactericidal agent are added thereinto; and wherein said perfume is banana essence.

6. The skin care product as defined in claim 1, wherein said detergent base is a powdered detergent base.

7. The skin care product as defined in claim 6, wherein said evening primrose powder has a particle size ranging between 90 and 120 mesh; wherein said powdered detergent base contains 75 parts of wheat powder, 15 parts of kaolin, 0.65 part of surfactant, 7 parts of boron sand, 2 parts of silicon dioxide, and 0.35 part of pigment; and wherein said perfume is pineapple essence.

* * * * *